United States Patent [19]
Buscemi et al.

[11] Patent Number: 5,443,495
[45] Date of Patent: Aug. 22, 1995

[54] POLYMERIZATION ANGIOPLASTY BALLOON IMPLANT DEVICE

[75] Inventors: Paul J. Buscemi, Long Lake; Andrew W. Buirge, Minneapolis; Fertac Bilge, Arden Hills, all of Minn.

[73] Assignee: Scimed Lifesystems Inc., Maple Grove, Minn.

[21] Appl. No.: 122,158

[22] Filed: Sep. 17, 1993

[51] Int. Cl.⁶ .................... A61F 2/06; A61M 29/00
[52] U.S. Cl. .......................... 623/1; 606/191; 604/96
[58] Field of Search ............. 604/96, 103; 623/1; 606/191-195

[56] References Cited

U.S. PATENT DOCUMENTS

| | | |
|---|---|---|
| 3,056,408 | 4/1959 | Brown . |
| 4,230,119 | 10/1980 | Blum . |
| 4,402,319 | 9/1983 | Handa et al. .......... 606/195 |
| 4,404,971 | 9/1983 | LeVeen et al. . |
| 4,503,569 | 3/1985 | Dotter . |
| 4,661,095 | 4/1987 | Taller et al. .......... 604/103 |
| 4,714,450 | 12/1987 | Calperon .............. 604/28 |
| 4,763,653 | 8/1988 | Rockey . |
| 4,776,337 | 10/1988 | Palmaz . |
| 4,795,458 | 1/1989 | Regan . |
| 4,820,298 | 3/1989 | Leveen et al. . |
| 4,830,003 | 5/1989 | Wolff et al. . |
| 4,832,688 | 5/1989 | Sagae et al. . |
| 4,840,690 | 6/1989 | Melinvshyn et al. . |
| 4,877,030 | 10/1989 | Beck et al. . |
| 4,878,492 | 11/1989 | Sinofsky et al. ......... 623/1 |
| 4,886,062 | 12/1989 | Wiktor . |
| 4,900,303 | 2/1990 | Lemelson . |
| 4,922,905 | 5/1990 | Strecker . |
| 4,923,464 | 5/1990 | DiPisa, Jr. . |
| 4,929,240 | 5/1990 | Kirsch et al. . |
| 4,944,746 | 7/1990 | Iwata et al. ............ 606/195 |
| 4,950,227 | 8/1990 | Savin et al. . |
| 4,969,890 | 11/1990 | Sugita et al. . |
| 5,015,253 | 5/1991 | MacGregor . |
| 5,019,090 | 5/1991 | Pinchuk . |
| 5,037,427 | 8/1991 | Harada et al. . |
| 5,041,126 | 8/1991 | Gianturco . |
| 5,059,211 | 10/1991 | Stack et al. . |
| 5,078,736 | 1/1992 | Behl . |
| 5,089,005 | 2/1992 | Harada . |
| 5,092,839 | 3/1992 | Kipperman . |
| 5,092,841 | 3/1992 | Spears . |
| 5,092,877 | 3/1992 | Pinchuk . |
| 5,100,429 | 3/1992 | Sinofsky et al. . |
| 5,102,417 | 4/1992 | Palmaz . |
| 5,181,921 | 1/1993 | Makita et al. .......... 606/195 |
| 5,250,069 | 10/1993 | Nobuyoshi et al. ...... 606/192 |
| 5,286,254 | 2/1994 | Shapland et al. ....... 604/21 |
| 5,334,201 | 8/1994 | Cowan ................ 623/1 |
| 5,344,419 | 9/1994 | Spears . |
| 5,344,444 | 9/1994 | Glastra . |
| 5,352,199 | 10/1994 | Tower ................. 604/96 |
| 5,520,823 | 6/1985 | LeVeen et al. . |

FOREIGN PATENT DOCUMENTS

| | | |
|---|---|---|
| 0442657 | 8/1991 | European Pat. Off. ..... 623/1 |
| PCT/US90/-02406 | 4/1990 | WIPO . |
| 9116864 | 4/1991 | WIPO .................. 623/1 |

OTHER PUBLICATIONS

Polymers for Engineering Applications, p. 12.
8. Technora Aramid Fiber, p. 271.

*Primary Examiner*—David Isabella
*Assistant Examiner*—Laura Fossum
*Attorney, Agent, or Firm*—Vidas, Arrett & Steinkraus

[57] ABSTRACT

A balloon/stent device for enlarging in situ to fit against a vessel wall and hardening in place.

12 Claims, 3 Drawing Sheets

POLYMERIZATION ANGIOPLASTY BALLOON IMPLANT DEVICE

FIELD OF THE INVENTION

This invention relates generally to a polymerizable balloon for use in balloon angioplasty and other procedures involving balloon catheters. More particularly, this invention relates to a balloon of polymerizable material, the cylindrical body portion of which, or a sleeve thereon, is caused to harden after inflation of the balloon in a body vessel duct or the like to form a liner or stent therein.

BACKGROUND OF THE INVENTION

Development of the balloon angioplasty technique began about fifteen years ago. The purpose of this technique is to open arteries in which the flow of blood has been impeded by build-up of arteriosclerotic plaques on the interior walls of the arteries. This technique consists of inserting a small diameter catheter into a blocked artery, the catheter having a small flexible balloon attached to its distal end. The catheter is moved through the artery until the balloon is placed in the area of the artery in which blood flow is impeded by plaque build-up. The balloon is then inflated in order to shear and disrupt the wall components of the vessel to obtain an enlarged lumen. With respect to arterial arthrosclerotic lesions, the relatively incompressible plaque remains unaltered, while the more elastic medial and adventitial layers of the vessel stretch around the plaque, thus opening the artery to permit improved blood flow. The balloon is then deflated and removed leaving plaque flattened against the artery walls.

After a period of several months, however, approximately one-third of the treated arteries sometimes undergo restenosis or a reclosing of the artery at the treated area, requiring repetition of balloon angioplasty. The restenosis problem has received considerable attention and several proposals have been made to deal with it.

The most promising approach to restenosis prevention has been the placement of a stent in a blood vessel which has undergone balloon angioplasty at the position in the vessel where the balloon was inflated. The stent is generally implanted inside a body vessel in a procedure immediately following the balloon angioplasty procedure. A stent (also referred to as a graft prosthesis, arterial endoprosthesis, intraluminal graft or intravascular mechanical support) is typically placed or implanted within the vascular system to reinforce collapsing, partially occluded, weakened or abnormally dilated localized sections of blood vessels or the like. Because stents generally have too large a diameter to fit through a pre-angioplasty, unexpanded, diseased portion of a vessel, conventional metal stenting procedures implant a stent or other intraluminal vascular graft subsequent to the initial balloon angioplasty procedure in which the vessel has been expanded. The simultaneous placement of a stent during the primary dilatation phase of a balloon angioplasty or other procedure would alleviate the restenosis problems and the need for a two-step procedure wherein the angioplasty procedure is performed first, followed by the stent placement procedure.

Another disadvantage of balloon angioplasty is the tendency of the balloon to adhere to the vessel wall during the dilatation phase of the angioplasty procedure. If a balloon adheres to a vessel wall, the procedure could produce dissection, or a splitting and tearing of the vessel wall layers, wherein the intima or internal surface of the vessel suffers fissuring. This dissection forms a "flap" of underlying tissue which may reduce the blood flow through the lumen, or block the lumen altogether. Typically, the distending intraluminal pressure within the vessel can hold the disrupted layer or flap in place. If the intimal flap created by the balloon dilation procedure is not maintained in place against the expanded intima, the intimal flap can fold down into the lumen and close off the lumen or become detached. When the intimal flap closes off the body passageway, immediate surgery is necessary to correct this problem. Thus, the adhesion of the balloon to the vessel wall can cause undesirable defects or irregularities in the wall surface, resulting in thrombosis, and restenotic episodes.

It would be advantageous to be able to provide a liner or a stent to cover and reinforce the interior portion of the vessel with a material that would provide a non-thrombogenic protective and supporting surface. Ideally, this protective liner would be provided during the primary dilatation phase of the angioplasty procedure rather than after the initial expansion of the vessel wall as in conventional angioplasty procedures. Thus, it would be extremely advantageous if the balloon itself, or a sleeve encasing the balloon, could be converted into a device capable of overcoming the two previously mentioned disadvantages: resentosis and adhesion.

SUMMARY OF THE INVENTION

In one aspect, the present invention is an angioplasty balloon having a cylindrical body portion adapted to harden in an enlarged state within a body vessel after the primary dilatation phase of a balloon angioplasty procedure. In another aspect, the present invention is a balloon sleeve adapted to cylindrically encase a conventional angioplasty balloon, thereby protecting the balloon and giving it a low profile for insertion into and through the diseased portion of a vessel, the sleeve being adapted to enlarge upon inflation of an angioplasty balloon and to harden in an enlarged state such that the balloon sleeve covers and provides mechanical support to the luminal surface of the vessel after removal of the angioplasty balloon. In short, both aspects of the invention provide a stent which can be placed simultaneously with the primary dilatation phase of the angioplasty procedure. The device may also be used to create or sustain openings or vessels in the renal, urinary, hepatic organs or other vessels, ducts and the like.

DETAILED DESCRIPTION OF THE DRAWINGS AND THE PREFERRED EMBODIMENTS OF THE INVENTION

One approach according to this invention for the percutaneous repair of cardiovascular anomalies is that the balloon itself may become a stent if it is released from the catheter by separation of the central body from the end cones. An extension of this approach is to make a balloon that hardens in the middle and degrades at the ends upon delivery.

Such a device would be delivered to the desired portion of vasculature in the usual manner for a percutaneous dilatation. The actual device would closely resemble a percutaneous transliminal coronary angioplasty ("PCTA") balloon catheter. After the device was positioned, it would be inflated so that the body of the balloon would come in contact with the vessel wall. At this point, energy would be supplied to the balloon through the catheter, in the form of heat or light, causing the center (cylindrical) portion of the balloon body to harden while the ends would dissolve or degrade away. The ends may also be made to detach from the cylindrical body of the balloon by the degradation of an adhesive or the like holding the cone ends to the balloon body initiated by the delivery of energy. Thirdly, the ends of the balloon may be made to detach by shrinking away from the hardening balloon section and adhering to the shaft of the catheter upon delivery of the energy. The implanted portion of the balloon provides support for the vasculature and/or may be a drug delivering matrix. The implanted section of the balloon may be biodegradable, thus eventually being resorbed into the body.

Another approach comprises a sleeve which encases an ordinary PTCA balloon. The sleeve would be the equivalent of the balloon body described above. After hardening the sleeve, the balloon would be deflated and removed, leaving the sleeve in place.

Figure 1:
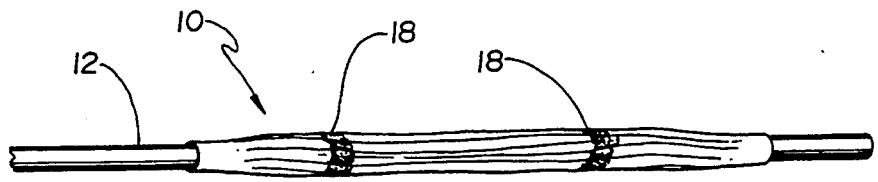
FIG. 1 is a portrayal of a balloon in the folded or wrapped conformation. The balloon deflated and stretched slightly to form essentially longitudinal creases in the balloon. The darkened regions (B) of the balloon represent regions of the balloon material which are chemically altered to degrade under the influence of heat or light. Regions A, B, C of the balloon may be of differing chemical compositions to allow either stiffening or degradation of the material.
Figure 2:
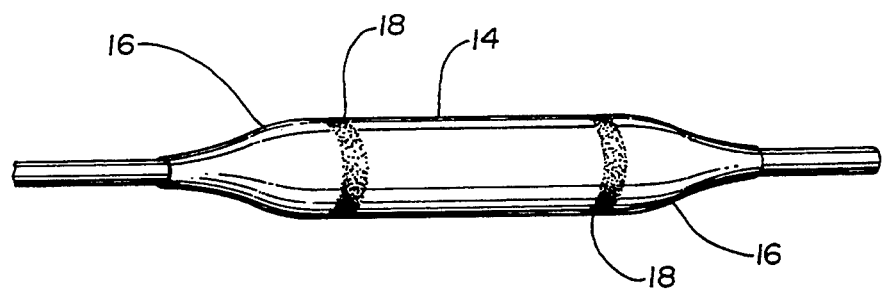
FIG. 2 shows the balloon of FIG. 1 in inflated form to approximately one to 12 arms atmospheres. All portions of the balloon inflate uniformly despite the differing chemical compositions.
Figure 3:
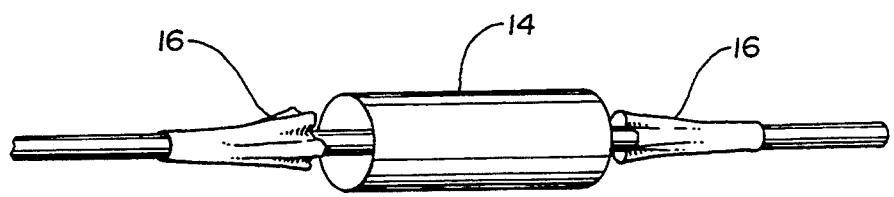
FIG. 3 shows the balloon of FIGS. 1 and 2 after the application of heat or light energy that has activated regions B and C. Region B has disintegrated; region C has become more rigid. The catheter shaft and the attached cones are withdrawn through the placed stent.

FIG. 1 illustrates an angioplasty balloon of the first preferred embodiment of the present invention. The balloon, shown generally by 10 is incorporated into a conventional angioplasty balloon catheter 12 by being wrapped about the catheter as shown for insertion into the lumen of a vessel. The balloon as seen in FIG. 2 in an inflated condition comprises a cylindrical body portion 14 and two end or cone portions 16. In use, the balloon is positioned in the area of a vascular lesion and is thereafter inflated. After inflation, energy is supplied to the balloon, causing the cylindrical body portion 14 of the balloon to harden while simultaneously causing the cone portions 16 of the balloon to dissolve or degrade or otherwise separate from body 14 as seen in FIG. 3. The cylindrical body portion 14 of the balloon, in its enlarged state, lies against the luminal surface of the vessel wall, providing mechanical support thereto. The body portion of the balloon provides the vessel wall with a protective, non-thrombogenic surface during the primary dilatation phase of the angioplasty procedure, while also acting as a stent. The catheter along with end portions or cones 16 is withdrawn through the emplaced stent.

The material comprising the body portion 14 of the balloon 10 is made to undergo a transformation such that it becomes rigid and inelastic upon the application of appropriate energy thereto. Upon transformation, the material comprising the body portion of the balloon remains within place in the vessel due to its tight fit. It may also adhere to the luminal surface of the vessel wall. A prepolymer is a material containing polymerizable groups such as acrylate or methacrylate. Acrylated or methacrylated materials such as polyethylene glycol (PEG) dimethacrylate, isobornyl acrylate, and neopentyl glycol diacrylate are all prepolymers. These materials, when in the presence of 2-hydroxy-2-methyl-1-phenylpropan-1-one and irradiated with ultraviolet light, will form a crosslinked, insoluble polymer matrix. For example, the hardenable balloon material may be a mixture of poly-D-L-lactic acid, (polymer), polyethylene glycol dimethacrylate (prepolymer) and isobornyl acrylate, neopentyl glycol diacrylate and/or 2-hydroxy-methyl-1-phenylpropan-1-one (initiators). Other initiator materials which are able to produce free radial bearing fragments upon irradiation may also be used. Such radical compositions are UV hardenable. A second balloon material can be formulated from all the above components, with the substitution of poly-DL-lactic acid or polycaprolactone for poly-L-lactic acid as the polymer. The crosslinking component need not be physically separate from the predominant polymer. It could be attached to the backbone or a sidechain, or the end of the polymer. Non degradable polymers as well as polyanhydrides. Polyphosphazines and other aliphatic could be interdeposed to form copolymers with the lactides and glycolides. Copolymers may be formed with carbohydrates and other biocompatible molecules. Radiation from a UV laser catheter introduced through a lumen of a balloon catheter via an optical fiber may be used to supply the requisite energy to polymerize the material.

Other pre-polymer examples:

--- ethylene glycol dimethacrylate
cyclohexyl methacrylate
diethylene glycol diacrylate
diethylene glycol dimethacrylate
neopentyl gylcol diacrylate
polyethylene glycol (600) dimethacrylate
tripropylene glycol diacrylate
lauryl methacrylate
stearyl methacrylate
ethoxylated bisphenol A dimethacrylate
ethoxylated bisphenol A diacrylate
di-trimethylol propane tetraacrylate (LTX)
isodecyl acrylate -continued dipert acrythritol pentaacrylate
isobornyl methacrylate
ethoxylated trimethylol propane triacrylate (LTX)
highly ethoxylated bispenol A dimethacrylate
propoxylated trimethylol propane triacrylate
dodecyl methacrylate
ethoxylated pentaerythritol tetraacrylate
caprolactone acrylate
highly ethoxylated TMPTA (trimethylolpropane triacrylate)
highly propoxylated TMPTA
highly ethoxylated TMPTA
bobrnyl acrylate
propoxylated neopentyl glycol diacrylate
glyceryl propoxy triacrylate
highly propoxylated gylceryl triacrylate
acrylated or methacrylated metabolic fragments dervied from reduction of Krebs diacids and subsequent esterification The material comprising the body portion 14 may contain activating agents which are incorporated directly into the polymer material. Examples of such activating agents include peroxides, azides, and other UV activated or heat activated agents as known in the art. The activating agents are incorporated into the polymer material and allow the polymer material to rapidly cross-link upon exposure to an activating energy source, such as fiber optic light. The energy will initiate the polymerization and/or cross-linking reaction to occur. The polymerization and or cross-linking causes the sleeve material to form a hardened or rigid material capable of supporting the interior surface of the lumen for an indefinite period of time. The transformation from flexible to rigid and self supporting causes the central balloon portion to stay in place.

The polymerization and/or cross-linking of the material of body portion 14 causes an increase in the modulus elasticity of the material from values typical of soft polymers, i.e., 0.1 GPa (Gigapascal) to that of stiffer molecules with moduli elasticity near 4.0 GPa for example. When the activating agents are located on the outside surface of the balloon, the polymerization and/or cross-linking reaction takes place on the surface of the vessel itself. This allows for bonding of the surface agents to both the polymer and the vessel wall.

Lower concentrations of polymerization and/or cross-linking agents on the lumen or interior side of the balloon cause that portion to degrade density enhances blood compatibility of the outer layer of the balloon since rapidly degrading materials will prevent a protein, platelet or leukocyte accumulation.

In addition, the polymerization and/or cross-linking agents that cause the modulus of elasticity to increase within the bulk of the polymer may not necessarily be the same one or ones that are preferred on the outside surface of the balloon where actual contact with the vessel is made. Cross-linking agents may be part of the polymer chains or may be incorporated into the bulk of the polymer by exposing preferably the exterior surface to a solution of the agent or agents so that the exterior side develops a higher concentration of agents than the lumen side.

In another preferred embodiment of the present invention highly active cross-linking agents are encapsulated within micelles. When the body 14 of the balloon 10 is stressed, i.e., expanded by inflation of the balloon, the micelles collapse releasing the activating agents. Upon expansion, the stress in the inflating body portion will be the greatest in the outer layers. If the body portion of the balloon comprises multiple layers, it is thus preferable to concentrate the micelles in the outer layers of body portion. The micellar encapsulated material may also be released by other suitable forms of stress energy, such as ultrasonic disruption. Thus, after the body portion of the balloon is inflated, an ultrasonic probe or transducer is inserted through a lumen in the catheter into or near the balloon cavity and activated, causing the release of activating agents. An example of such a system would be the incorporation of methylene diisocyanates (MDI) contained within phospholipid micelles composed of sodium dodecysulfate. The MDI micelles would be incorporated as an oil or oil in water emulsion into the stent material, which in this case may contain reactive amine groups, when it was cast from solution so that the micelles would not be physically stressed. Upon expansion of the balloon, the walls of the stent become thinner in proportion to the expansion of the stent. The shear stress placed on the micelles would cause them to burst or otherwise crack. The MDI would immediately react with the amines to crosslink the polymer comprising the stent.

Alternatively the micelles could be comprised of phosphatidylethanolamine or any other short chain polymer that would form micelles or microparticles. If the micelles contained peroxides or other free radical producing agents and if the polymer contained reactive double bonds as acrylates, then upon stressing the micelles, the free radicals would cause crosslinking of the polymer to occur. Alternately, the transducer may be the balloon itself which is then activated to release the micellar encapsulated activating agents. To accomplish this, the balloon may be comprised of a piezoelectric material as PVDF (e.g. polyvinylidinefluoride) that is electrically connected to a power source at the proximal end of the catheter. Upon the application of an alternating voltage, the polymer will vibrate in response to the polarity of the voltage and in accordance to how the material was polled (dipoles set).

The balloon of the first preferred embodiment of the present invention as shown in FIGS. 1–3 is incorporated into a catheter device which closely resembles a conventional percutaneous translumial coronary angioplasty ("PCTA") balloon catheter. The balloon is delivered to the desired portion of the vasculature in the usual manner for a percutaneous dilation. After the balloon is properly positioned in the area of the vascular lesion, it is inflated so that the balloon contacts and pushes back the material, generally plaque, which lines the vessel wall. Once the balloon is sufficiently inflated, energy is supplied to the balloon. The energy, preferably in the form of heat or light, causes the center body portion of the balloon to harden. The cones or ends 16 separate as described below and catheter 12 is then removed from the body as shown in FIG. 3, leaving the hardened body portion 14 of the balloon inside the vessel to provide mechanical support and to cover the vessel in order to prevent the formation of thrombus. The result is an in situ formed stent.

Figure 8:
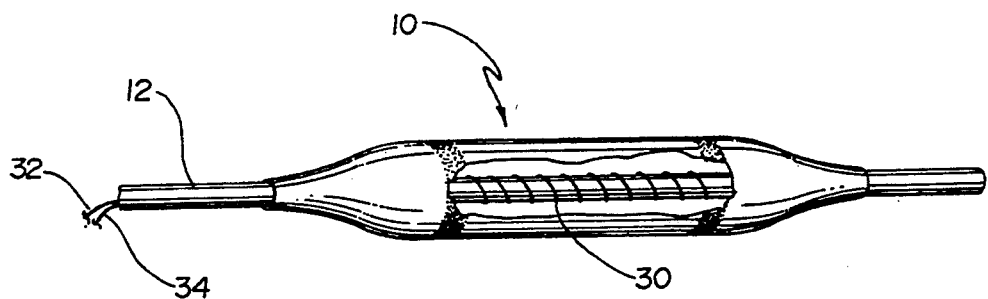
FIG. 8 shows a balloon with a resistance heating element.

Energy may be delivered to the stent during its formation in the following manner. If the energy is thermal the inner shaft of the balloon may be coated with a semiconductive material or wrapped with a wire resistance heating element 30 as shown in FIG. 8 such that, upon application of a current through leads 32 and 34, resistive heating occurs. The energy is conductively transferred to the surface of the balloon by the liquid filling the balloon (not shown).

Figure 9:
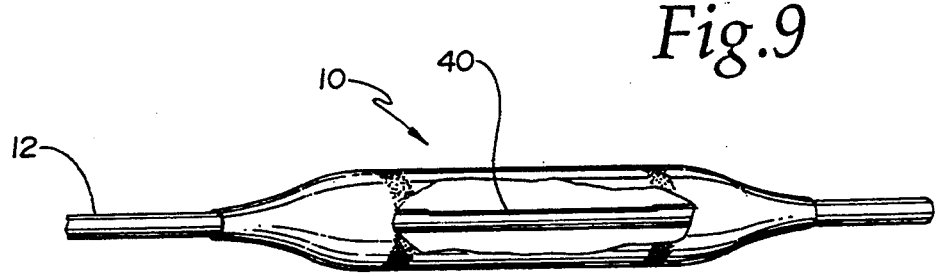
FIG. 9 shows a balloon with a radiation diffusing optical fiber.
Figure 10:
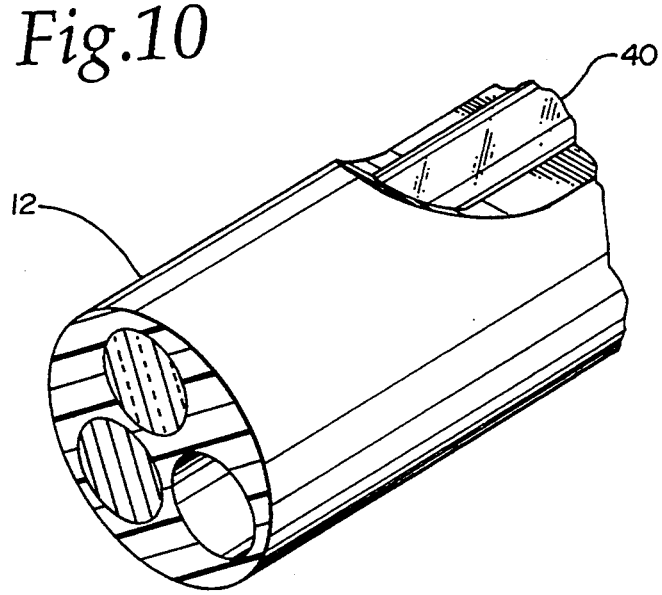
FIG. 10 is an enlarged portion of FIG. 9.

If the material in the stent or sleeve is activatible by light energy, then the center shaft of the catheter will contain an optic fiber 40 as shown in FIGS. 9 and 10 for diffusing radiation outwardly through the balloon. The fiber may be made such that it will diffuse light transmitted down the optic fiber to the interior surface of the balloon. This light energy would be absorbed by the reactive species in the stent and induce the crosslinking of the polymer comprising the stent or the formation of an interpenetrating network. Alternatively, vibrational energy, delivered by a piezo element (not shown) placed in the center of the balloon, could be delivered to the fluid filling the balloon causing it to heat, or the balloon itself could be caused to vibrationally heat if it were piezoelectric in nature.

In the first preferred embodiment of the balloon of the present invention shown in FIGS. 1–3, the cone or end portions 16 of the balloon spontaneously dissolve or degrade and separate from body 14 upon the application of energy thereto while the body portion 14 hardens.

The hardenable balloon body material is preferably a mixture of poly-L-lactic acid (molecular weight>1.4M), polyethylene glycol(Mw=600) dimethacrylate, isobornyl acrylate, neopentyl glycol diacrylate, and 2-hydroxy-2-methyl-1-phenylpropan-1-one. A second preferred balloon body material may be formulated from all the above components, with the substitution of poly-DL-lactic acid or poly caprolactone for the poly-L-lactic acid.

The end or cone portions 16 of the balloon may comprise a polymer which has labile components adapted to cause a chain scission reaction or may incorporate a polymer which are cleaved by a secondary, energy activated compound and which break down into components which are soluble and disperse. The polymers which may be used for the end portions of the balloon can be natural, synthetic or a modified natural polymer such as a conjugated protein. An example of a material for the scission regions 18 is a linear polyester prepared from 2-hydroxy-1-[4-(2-hydroxyethoxy)phenyl]-2-methyl-1-propanone, dimethyl succinate and zinc stearate. Along with the linear polyester is mixed 4-methoxyphenol. A second polymer would be a linear polyester prepared from 2-hydroxy-1-[4-(2-hydroxyethoxy)-phenyl]-2-methyl-1-propone, dimethyl fumarate, dimethylsebacate, and zinc stearate mixed with 4-hydroxyphenyloctyl ether.

In another embodiment, the cones of a balloon may detach from the cylindrical body of the balloon by the degradation of material at the scission regions 18 (See FIG. 2) attaching the cones 16 to the body 14. The degradation is initiated by the application of energy from the catheter. In yet another embodiment, the cones 16 of the balloon 10 detach by shrinking away from the hardening body section 14 of the balloon and adhere to the shaft 12 of the catheter upon delivery of energy as seen in FIG. 2. Such an arrangement is made possible if the cones are made of polyethylene, or polyolefin copolymer that has been formed into a cone. In such an embodiment, the cone material changes its physical properties sufficient to become soft and easily pulled away from the hardened balloon portion upon the application of energy thereto.

In order to provide a conventional angioplasty balloon with a low profile and to protect it from tearing, many manufacturers often wrap or coil a conventional angioplasty balloon inside a protective tube or sleeve, which is removed from the balloon prior to the procedure. It would be extremely advantageous if the protective sleeve did not have to be removed but could serve an additional purpose, such as a stent. This is provided by the second embodiment of this invention as seen in FIGS. 4–5.

Figure 4:
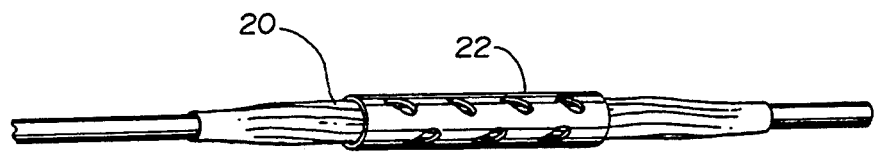
FIG. 4 shows a chemically alterable stent loaded onto a folded balloon for delivery. The stent may contain slits or holes or slots which expand when the balloon expands the stent.

In that embodiment of the present invention, a conventional angioplasty balloon 20, see FIG. 4, is folded and encased in a balloon sleeve 22 comprising a material having the same properties as the body portion 14 of the balloon 10 described above in connection with FIGS. 1–3. The sleeve 22 cylindrically encases a conventional angioplasty balloon 20, giving the balloon 20 a low profile for insertion into a diseased area and protects the balloon from ripping or tearing.

Figure 5:
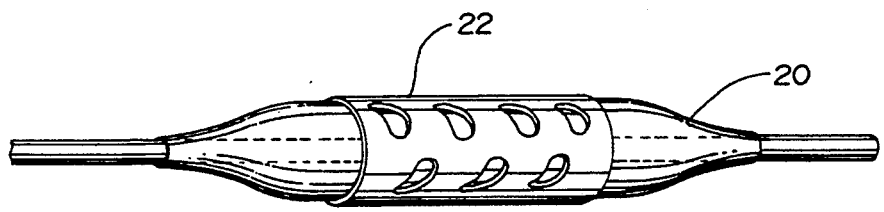
FIG. 5 shows the expanded stent of FIG. 4 on inflated balloon. The slots have increased in open area. The cross sectional area of the stent has decreased with the increase in diameter. The stent is activated by light or heat to cause an increase in stiffness.

In use, the balloon 20 encased in the sleeve 22 is positioned adjacent the diseased portion of the vessel and is enlarged from a first insertion diameter to a second enlarged diameter as shown in FIG. 5 upon expansion of the balloon. Thereafter, the sleeve 22 is caused to harden or become rigid in its enlarged state. The sleeve material stretches during the primary expansion phase, conforming first to the shape of the balloon and then, as the balloon impinges on the vessel wall, to the shape of the combination of the balloon and wall.

The sleeve 22 is generally cylindrical in shape as seen in FIGS. 2 and 3 and is comprised of a polymer material which is capable of stretching to and maintaining a second, enlarged diameter configuration. The sleeve is formed by immersion of a mandrel in a solution or by spraying a mandrel. The transformation of the sleeve material to a rigid or hardened state can be induced by any of the methods previously described. Thus, the application of energy may be used to initiate polymerization and cross-linking reactions, which causes the sleeve material to harden. Alternately, the transformation may also be caused by the release of chemical components encapsulated in the wall of the sleeve induced by stretching or the application of energy.

Figure 6:
FIG. 6 shows a stent as in FIG. 4a except that in place of slots or slits, the stent is comprised of a microporous material, which again increases in cross sectional area as the balloon expands the stent.
Figure 7:
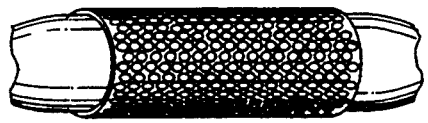
FIG. 7 shows the balloon of FIG. 6 expanded.

FIGS. 6 and 7 show a stent as in FIG. 4 except that in place of slots or slits, the stent is comprised of a microporous material in which the slots or slits increase in cross sectional area as the balloon expands the stent.

In order to perform both functions, i.e., encasing the balloon and as an arterial lining, the sleeve material must be able to maintain sufficient strength to keep the folds of the balloon in place. It must also be capable of being expanded by the balloon without the addition of any form of energy prior to expansion, since this may lock the unexpanded sleeve in place. The sleeve will be relatively thin walled and sufficiently flexible to negotiate bends and curves encountered in the coronary and other arteries. The sleeve will generally range before expansion from about 1 mm to 3 mm ID with wall thickness typically ranging from about 0.1 to 0.5 min. The wall thickness will decrease depending on the expansion of the sleeve. Also, the thickness will decrease in proportion to the differences determined by Area=$pi(r1^2-r2^2)$ where r1 and r2 are the inner and outer radius, generally speaking.

The sleeve may be comprised of a single polymeric material or multiple layers of different polymeric materials. A sleeve comprising multiple layers may, for example, include an interior layer of a non-adhesive swellable hydrogel such as collagen or polyvinylpyrrolidone which is suitable for release from the balloon surface, one or more middle layers such as polylactic acid (PLA), specifically poly-L-lactic acid (PLLA), and cross-linking which are suitable for uniform expansion under stress (plastic and formation) and cross-linking and an exterior layer such as collagen or other polyesters, which are suitable for adhesion to the vessel wall by cross-linking or the like. In addition, the sleeve may comprise a polymer or polymers which contain therapeutic or pharmacological agents incorporated thereon.

Both the polymerizable balloon and sleeve embodiments of the present invention may comprise materials such as PLA which will biodegrade after a predetermined amount of time and/or may comprise materials capable of releasing drugs or other pharmaceuticals into the surrounding tissue.

It should be appreciated that the device and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by all the appended claims rather than by the foregoing description. All changes which come within the meaning and range of equivalency of the claims are to be embraced with their scope.

What is claimed is as follows:

1. A balloon for catheters, the balloon comprising a body portion and two end portions, the balloon being inflatable from a first condition to a second enlarged condition, and wherein:
   a) said body portion of the balloon is made of a material which will undergo a transformation from a flexible, elastic condition to a rigid, inelastic condition upon an application of energy thereto; and
   b) said two end portions detach from said body portion by a degradation of a scission material, said degradation initiated by the application of energy thereto.

2. The device of claim 1 wherein the body portion comprises a prepolymer containing polymerizable groups.

3. The device of claim 2 wherein the polymerizable groups are selected from the group consisting of acrylates and methacrylates.

4. The device of claim 2 wherein the body portion further comprises activating agents.

5. A balloon for use on a catheter having a shaft, the balloon comprising a body portion and two end portions, the balloon being inflatable from a first condition to a second enlarged condition, and wherein:
   a) said body portion of the balloon is made of a material which will undergo a transformation from a flexible, elastic condition to a rigid, inelastic condition upon an application of energy thereto; and
   b) said end portions detach from said body portion and adhere to the shaft of the catheter upon application of energy thereto.

6. A balloon for catheters, the balloon comprising a body portion and two end portions, the balloon being inflatable from a first condition to a second enlarged condition, wherein:
   a) said body portion of the balloon is made of a material which will undergo a transformation from a flexible, elastic condition to a rigid, inelastic condition and said end portions comprise a material which will degrade, both transformations occurring upon an application of energy to the balloon; and
   b) said body portion contains a mixture of poly-D-L-lactic acid, polyethylene glycol dimethacrylate, isobornyl acrylate, neopentyl glycol diacrylate and 2-hydroxy-methyl-1-phenylpropan-1-one.

7. A balloon for catheters, the balloon comprising a body portion and two end portions, the balloon being inflatable from a first condition to a second enlarged condition, wherein:
   a) said body portion of the balloon is made of a material which will undergo a transformation from a flexible, elastic condition to a rigid, inelastic condition and said end portions comprise a material which will degrade, both transformations occurring upon an application of energy to the balloon; and
   b) said body portion contains a mixture of poly-L-lactic acid, polyethylene glycol dimethacrylate, isobornyl acrylate, neopentyl glycol diacrylate, and 2-hydroxy-2-methyl-1-phenylpropan-1-one.

8. A balloon for catheters, the balloon comprising a body portion and two end portions, the balloon being inflatable from a first condition to a second enlarged condition, wherein:
   a) said body portion of the balloon is made of a material which will undergo a transformation from a flexible, elastic condition to a rigid, inelastic condition and said end portions comprise a material which will degrade, both transformations occurring upon an application of energy to the balloon; and
   b) the body portion comprises:
      i) a prepolymer containing polymerizable groups; and
      ii) activating agents selected from the group consisting of peroxides and azides.

9. A balloon for catheters, the balloon comprising a body portion and two end portions, the balloon being inflatable from a first condition to a second enlarged condition, wherein:
   a) said body portion of the balloon is made of a material which will undergo a transformation from a flexible, elastic condition to a rigid, inelastic condition and said end portions comprise a material which will degrade, both transformations occurring upon an application of energy to the balloon; and
   b) the body portion comprises:
      i) a prepolymer containing polymerizable groups; and
      ii) activating agents encapsulated in micelles.

10. A balloon for catheters, the balloon comprising a body portion and two end portions, the balloon being inflatable from a first condition to a second enlarged condition, wherein:
    a) said body portion of the balloon is made of a material which will undergo a transformation from a flexible, elastic condition to a rigid, inelastic condition and said end portions comprise a material which will degrade, both transformations occurring upon an application of energy to the balloon; and
    b) the end portions contain a mixture of a linear polyester prepared from 2-hydroxy-1-[4-(2-hydroxyethoxy)phenyl]-2-methyl-1-propanone, dimethyl succinate and zinc stearate, and 4-methoxyphenol.

11. A balloon for catheters, the balloon comprising a body portion and two end portions, the balloon being inflatable from a first condition to a second enlarged condition, wherein:

a) said body portion of the balloon is made of a material which will undergo a transformation from a flexible, elastic condition to a rigid, inelastic condition and said end portions comprise a material which will degrade, both transformations occurring upon an application of energy to the balloon; and b) the end portions contain a mixture of a linear polyester prepared from 2-hydroxy-1-[4-(2-hydroxyethoxy)phenyl]-2-methyl-1-propanone, dimethyl fumarate, dimethylsebacate and zinc stearate, and 4-hydroxyphenyloctyl ether.

12. A balloon for catheters, the balloon comprising a body portion and two end portions, the balloon being inflatable from a first condition to a second enlarged condition, wherein:

a) said body portion of the balloon is made of a material which will undergo a transformation from a flexible, elastic condition to a rigid, inelastic condition and said end portions comprise a material which will degrade, both transformations occurring upon an application of energy to the balloon; and b) the body portion is biodegradable.

* * * * *